United States Patent [19]

Mimura

[11] Patent Number: 4,998,918
[45] Date of Patent: Mar. 12, 1991

[54] CONTINUOUS INJECTOR OF LIQUID MEDICINE

[75] Inventor: Shinji Mimura, Saitama, Japan

[73] Assignee: Kabushiki Kaisha Mimura Sogo Kenkyuusho, Japan

[21] Appl. No.: 374,017

[22] Filed: Jun. 30, 1989

[51] Int. Cl.⁵ ............................................ A61M 37/00
[52] U.S. Cl. .................................................. 604/132
[58] Field of Search .............. 604/131, 132, 135, 118, 604/247, 248, 257

[56] References Cited

U.S. PATENT DOCUMENTS 4,202,333  5/1980  Thill et al. ........................ 604/135
4,741,733  5/1988  Winchell et al. .................. 604/132

FOREIGN PATENT DOCUMENTS 61-51901  11/1986  Japan .
62-11464  1/1987  Japan .
62-11465  1/1987  Japan .

Primary Examiner—John D. Yasko
Attorney, Agent, or Firm—Lowe, Price, LeBlanc, Becker & Shur

[57] ABSTRACT

A continuous liquid medicine injector has a cylindrical body. A liquid medicine receiving portion is provided at one end of the cylindrical portion, and an instrument inserted into a human body which may be a needle is provided at the other end thereof. Two ends of a tubular rubber-like elastic film are fixed to an intermediate portion of the cylindrical body. A liquid medicine flow into the elastic film through a through-hole formed in the cylindrical body to inflate the elastic film, and the elastic film which has been inflated forms a pressurizing means of the liquid medicine. A thin tube having a predetermined inner diameter and a predetermined length is disposed within the cylindrical body. One end of the thin tube is made to communicate with the instrument inserted into the human body.

13 Claims, 4 Drawing Sheets

CONTINUOUS INJECTOR OF LIQUID MEDICINE

BACKGROUND OF THE INVENTION

1. Filed of the Invention

The present invention relates to a continuous liquid medicine injector for sequentially injecting a liquid medicine, accommodated in a liquid medicine accommodating portion, into a human body. More particularly, the present invention concerns an improvement in a means for controlling the flow rate of a liquid medicine which is injected from a liquid medicine accommodating portion into a human body.

2. Description of the Related Art

Methods of continuously injecting a liquid medicine into a human body are known. In one such method, a liquid medicine in an injector is manually or automatically supplied into the body through a needle or a catheter. In another method, a liquid medicine in an instillator is naturally or automatically supplied into the body.

In all of the above-described injecting methods, it takes from a few minutes to a few hours for all the drugs to be injected. During that time, a needle or the like has to be connected to a syringe or the like, and this may cause pain to the patient or limit what he or she is able to do during the injection. It may also be necessary for the operator, who may be a doctor or a nurse, to hold a syringe or check the amount of liquid medicine given by an intravenous drip injection, making the injection procedure a troublesome task.

Accordingly, a small and easy-to-handle continuous liquid medicine injector (a catheter) which does not limit the actions of a patient or an operator has been proposed (in, for example, the specifications of Japanese Patent Publication No. 61-51901 and Japanese Patent Laid-Open Nos. 62-11464 and 62-11465).

All of these conventional continuous liquid medicine injectors incorporate a balloon made of an elastic material An inlet portion from which a liquid medicine is sucked into the balloon is provided at one end of the balloon, and an outlet portion from which the liquid medicine is forced out of the balloon is provided at the other end thereof The inlet portion is provided with a check valve which allows the liquid medicine to flow into the balloon but does not permit it to flow out of it. In the conventional continuous liquid medicine injector arranged in the above-described manner, the liquid medicine accommodated in the balloon is forced out of it from the outlet portion due to the contraction of the balloon and is caused to flow into the body through an instrument inserted into a human body such as a needle.

However, all of these continuous liquid medicine injectors involve a problem that the flow of liquid medicine cannot be controlled to a sufficient degree in the outlet portion. This has been an obstacle to practical use of these injectors.

More specifically, in the continuous injector disclosed in the specification of Japanese Patent Publication No. 61-51901, the flow of liquid medicine is controlled by suitably changing the diameter of through-holes formed in the wall of a tube-like body on which the balloon is mounted or by employing a diaphragm which varies the area of the inner diameter of the outlet portion of the tube-like body in accordance with the inner pressure of the balloon. However, control of the diameter of the through-hole formed in the tube wall does not ensure sufficient control of the flow rate due to the thinness of the tube wall. Also, the required diaphragm is difficult to manufacture and its use is therefore, not practical.

Furthermore, in the continuous injector proposed in the specification of Japanese Patent Laid-Open No. 62-11464, control of the flow of liquid medicine is performed by varying the diameter of a thin tube (thin hole) formed in the tube wall in the axial direction of a catheter. However, formation of a thin hole in the axial direction of the thin catheter is difficult, making precise control of the flow rate more difficult.

Furthermore, the continuous injector proposed in the specification of Japanese Patent Laid-Open No. 62-11465 incorporates a liquid medicine flow regulating valve in the outlet portion, and flow control is performed by controlling the restricting ratio of the flow regulating valve. However, precise control is also difficult in this injector, as in the former type of injector.

SUMMARY OF THE INVENTION

An object of the present invention is to provide a continuous injector for a liquid medicine which has a simple structure and which ensures precise control of the flow of liquid medicine.

To this end, the present invention provides a continuous injector of a liquid medicine which includes a flow control means for controlling the flow of a liquid medicine which is forced from a liquid medicine accommodating portion into an instrument inserted into a human body, such as a needle or a catheter, by means of a pressurizing means. The flow control means is a thin tube having a predetermined inner diameter and a predetermined length.

The thin tube employed in the present invention ma y be a resin, metal or ceramic tube having an accurately formed inner diameter and available on the market.

Furthermore, a covering tube with the thin tube bonded therein may be fixed to a cylindrical body that constitutes a liquid medicine accommodating portion Alternatively, the thin tube may be fixedly buried in a synthetic resin filling the cylindrical body which constitutes the liquid medicine accommodating portion. Alternatively, the thin tube may be fixed to the cylindrical body which constitutes the liquid medicine accommodating portion through end plates fixed to the two ends thereof.

Furthermore, a pressuring means may be a rubber-like elastic membrane mounted on the cylindrical body.

In the continuous liquid medicine injector according to the present invention, the flow control means includes a tube having an accurately formed inner diameter. In consequence, the flow of liquid medicine can be very easily controlled by suitably selecting a thin tube having a predetermined inner diameter and a predetermined length.

DETAILED DESCRIPTION OF THE PREFERRED EMBODIMENT

An embodiment of the present invention will be described below with reference to FIGS. 1 to 4.

Figure 1:
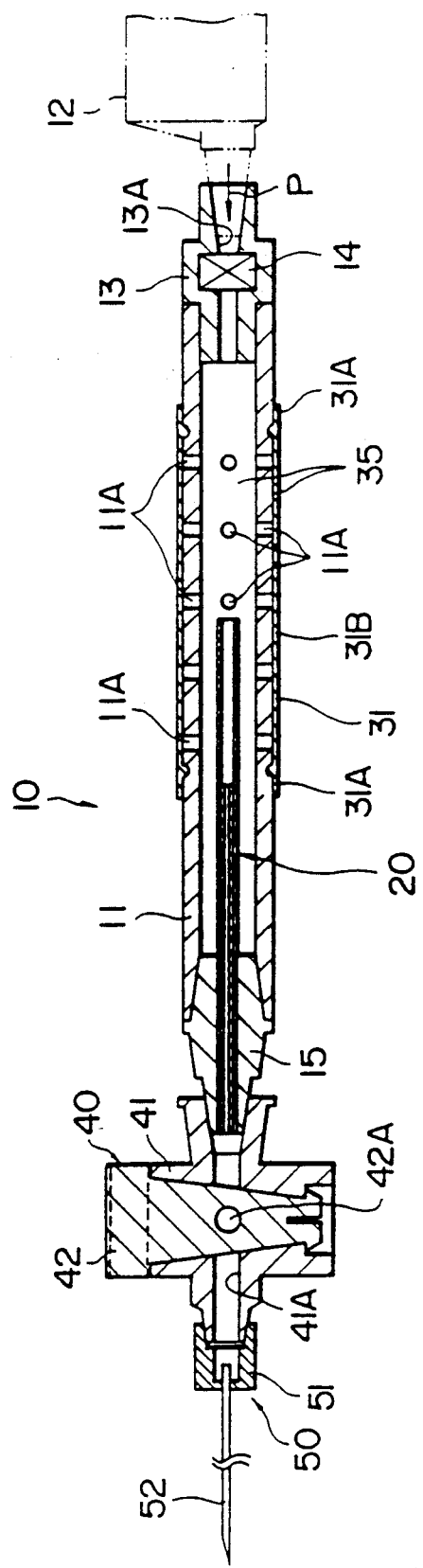
FIG. 1 is a cross-sectional view of an embodiment of the present invention.

Referring first to FIG. 1, a continuous injector 10 for a liquid medicine according to the present invention includes a cylindrical body 11 made of a synthetic resin or other material. It is preferable for the cylindrical body to be made of a transparent or translucent material from the viewpoint of affording visibility of the interior thereof.

At one end (the right end as viewed in FIG. 1) of the cylindrical body 11 is provided a liquid medicine receiving portion 13 of which a syringe 12 serving as a liquid medicine supply means can be mounted. The liquid medicine receiving portion 13 is provided with a liquid medicine flow-out prevention means 14 for preventing the liquid medicine which has been injected into the cylindrical body 11 from the syringe 12 from flowing out of the liquid medicine receiving portion 13. This liquid medicine flow-out prevention means 14 may be a check valve which permits the flow of the liquid medicine only in the direction indicated by the arrow P or a one-way cock which can open and close a flow passage 13A in the liquid medicine receiving portion 13. Any suitable check valve or one-way cock available on the market can be used.

Figure 2:
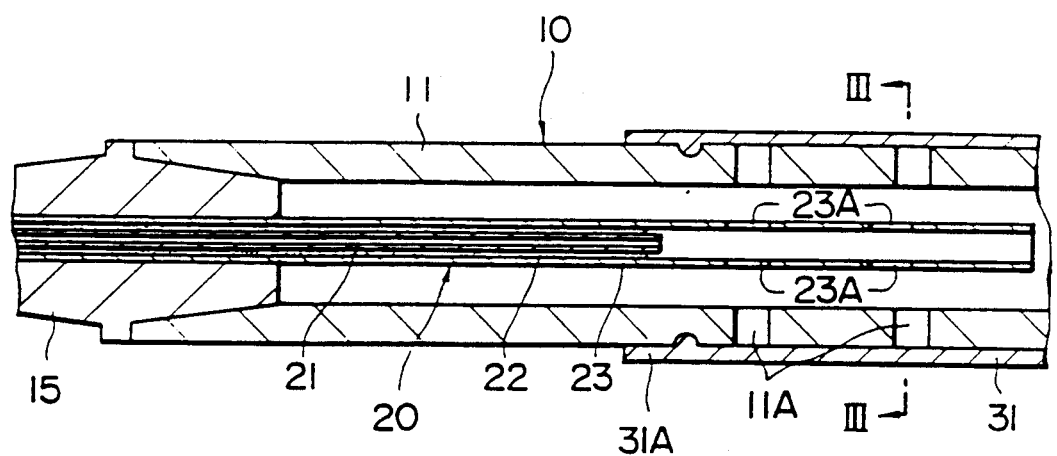
FIG. 2 is an enlarged cross-sectional view of the essential parts of the embodiment of FIG. 1.
Figure 3:
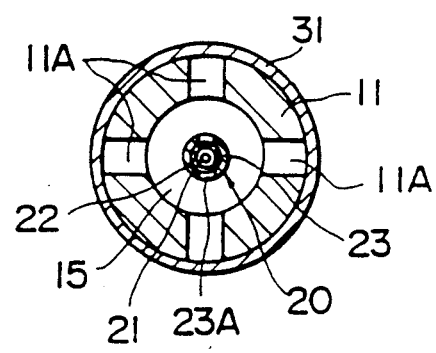
FIG. 3 is a section taken along the line III—III of FIG. 2.

At the other end (the left end as viewed in FIG. 1) of the cylindrical body 11 is a liquid medicine injecting portion 15 which is provided with a liquid medicine flow rate control means 20. As shown in FIGS. 2 and 3, the liquid medicine flow rate control means 20 includes a thin tube 21 having a very small inner diameter of, for example, 100 μm or 150 μm, and a covering tube 23 bonded to the outer periphery of the tube 21 by means of an adhesive 22 for covering the tube 21. The thin tube 21 is made of a resin, a metal or a ceramic. Any tube having an accurately formed inner diameter and available on the market can be employed.

One end of the covering tube 23 is inserted into the liquid medicine injecting portion 15 of the cylindrical body 11 and is hermetically fixed thereto The other end thereof protrudes from the thin tube 21. Through-holes 23A are formed in the tube wall that forms the protruding portion of the covering tube 23 so that the liquid medicine in the cylindrical body 11 can flow into the thin tube 21 therethrough.

A plurality of through-holes 11A are formed in the intermediate portion of the cylindrical body 11, and a cylindrical rubber-like elastic membrane 31 is mounted on the cylindrical body 11 in such a manner as to cover the portion of the cylindrical portion 11 in which the through-holes 11A are formed. The rubber-like elastic membrane 31 is fixedly attached to the outer periphery of the cylindrical body 11 in an air-tight manner at two end portions 31A thereof, an intermediate portion 31B thereof being separated from the outer periphery of the cylindrical body 11. The rubber-like elastic membrane 31 is made of an elastic material which is sufficiently wear resistant and tough as not to be readily damaged by any external force In particular, a transparent or translucent material which has the above-described properties is preferably employed. Suitable materials of the elastic membrane 31 include a silicone rubber and a latex rubber which are available on the market.

Figure 4:
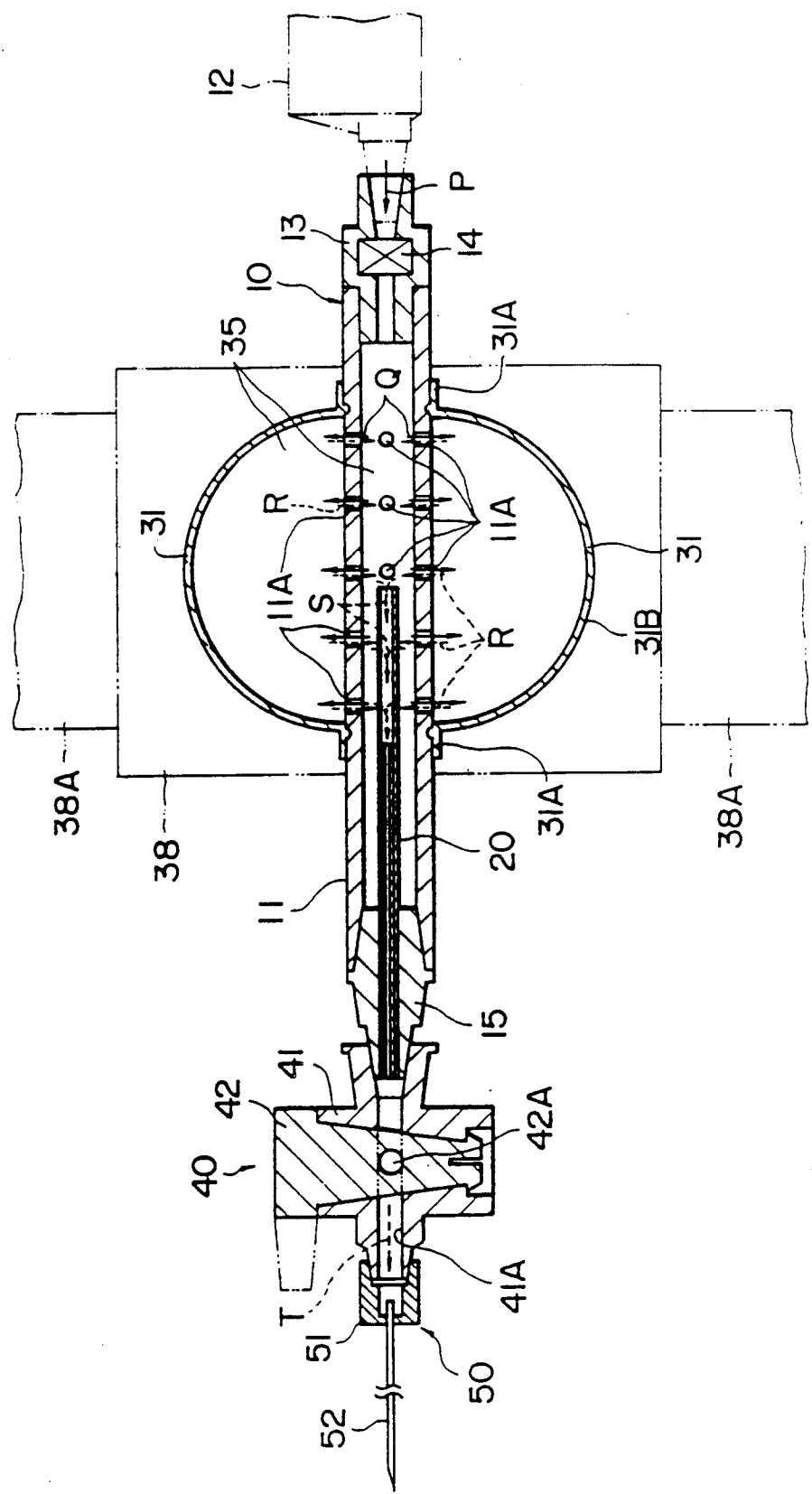
FIG. 4 is a cross-sectional view of the embodiment of FIG. 1; illustrating the operation thereof.

The rubber-like elastic film 31 is inflatable with the liquid medicine which flows thereinto through the through-holes 11A, as shown in FIG. 4. The rubber-like elastic membrane 31 which is inflated forms a liquid medicine pressurizing means. The interior of the inflated rubber-like elastic membrane 31 and that of the cylindrical body 11 constitute a liquid medicine accommodating portion 35.

At the outer end of the liquid medicine injecting portion 15 is detachably provided a cock 40 which serves as an opening/closing means. The cock 40 includes a body 41 with a flow passage 41A formed therein, body 41 being mounted on the liquid medicine injecting portion 15, and a knob 42 with a communication hole 42A which can communicate with the flow passage 41A formed therein, the knob 42 being pivotally mounted on the body 41. In consequence, the flow passage 41A can be blocked or made to communicate with the communication hole 42A by pivoting the knob 42. In the illustrations in FIGS. 1 and 4, the communication hole 42A is disposed perpendicular to the flow passage 41A to block it. Turning of the knob 42 through 90 degrees from the state illustrated opens the flow passage 41A.

A needle 50 which is an instrument inserted into a human body is detachably mounted on the body 41 of the cock 40. The needle 50, which is of type available on the market, includes a mounting portion 51 which can be mounted on the body 41 of the cock 40, and a needle 52 planted in the mounting portion 51

As shown in FIG. 4, a transparent cover 38, which covers the rubber-like elastic membrane 31 inflated in the form of a sphere, is mounted, if necessary. The cover 38 has a band 38A through which the cover 38 is mounted on the arm or the like of a patient. The cover 38 has the functions of protecting the rubber-like elastic membrane 31 in an inflated state and of fastening the injector onto the patient Next, the operation of the continuous injector arranged in the above-described manner will be described.

First , the cock 40, which is the opening/closing means, is mounted on the liquid medicine injecting portion 15 formed at one end of the cylindrical body 11 of the continuous liquid medicine injector 10, and the knob 42 of the cock 40 is operated in the manner illustrated in FIG. 1 to close it. In this state, the syringe 12, which is the liquid medicine supply means, is mounted on the liquid medicine receiving portion 13 of the cylindrical portion 11, and a predetermined amount of liquid medicine within the syringe 12 is forced out of it in the direction indicated by the arrow P.

The liquid medicine is forced into the cylindrical body 11 through the liquid medicine flow-out prevention means 14. At that time, since the cock 40 mounted on the liquid medicine injecting portion 15 of the cylindrical portion 11 is closed state the out flow of the liquid medicine from the liquid medicine injecting portion 15 is prevented, and this causes the liquid medicine in the cylindrical body 11 to flow in the direction indicated by the arrows Q shown by the solid lines in FIG. 4 and into the rubber-like elastic membrane 31 through the through-holes 11A, inflating the elastic membrane 21 in the form of a sphere. At that time, the contracting force of the elastic membrane 31 which is the reaction force caused by the inflation makes the rubber-like elastic membrane 31 serve as a pressurizing means which applies a predetermined amount of pressure to the liquid medicine. At the same time, the interior of the cylindrical body 11 and that of the elastic membrane 31 constitute the liquid medicine accommodating portion 35.

Further, the liquid medicine filling the rubber-like elastic membrane 31 is prevented from flowing back out of the liquid medicine receiving portion 13 by the action of the liquid medicine flow-out prevention means 14 provided in the liquid medicine receiving portion 13.

In a case wherein it is necessary for air to be prevented from entering the cylindrical body 11 and the rubber-like elastic membrane 31, the same type of liquid medicine or physiological salt solution may be injected in the cylindrical body 11 beforehand. Alternatively, the cylindrical body 11 is made upright with the liquid medicine injection portion 13 located upward after the injection of the liquid medicine In this way, bubbles in the rubber-like elastic membrane 31 and the cylindrical body 11 float up in the liquid medicine receiving portion 13 of the cylindrical portion 11, the air being readily discharged through a tube vent (not shown) inserted into the liquid medicine receiving portion 13 by opening the liquid medicine flow-out prevention means 14.

After a predetermined amount of liquid medicine has been injected into the continuous liquid medicine injector 10 in the manner described above, the needle 50, which is an instrument inserted into the human body, is mounted on the cock 40, this needle 50 being then inserted into the body, thereby completing the preparation of injection of liquid medicine into the human body.

Before the needle 50 is inserted into the body, air is discharged by causing a small amount of liquid medicine to flow out of the needle 50, if necessary. This is a normal air discharging operation.

After the insertion of the needle 50 into the body, the flow passage 41A is opened by turning the knob 42 of the cock 40 and thereby making the hole 42A communicate with the flow passage 41A. This causes the liquid medicine accommodated in the liquid medicine accommodating portion 35 in a state wherein it is being pressurized by the rubber-like elastic membrane 31 to flow in the direction indicated by the arrows R and S shown by the broken lines in FIG. 4 and into the liquid medicine flow rate control means 20 Thereafter, the liquid medicine in the liquid medicine flow rate control means 20 flows into the flow passage 41A of the cock 40 at a flow rate, i.e., in an amount, determined by the inner diameter and the length of the tube 21. The liquid medicine flows through the flow passage 41A in the direction indicated by the arrow T, then into a human body (not shown ) through the needle 50. At that time, since the flow rate of the liquid medicine is controlled by means of the liquid medicine flow rate control means 20, flow of the liquid medicine lasts for a predetermined period of time, in spite of the pressure applied to the liquid medicine by the rubber-like elastic membrane 31 which has been inflated.

The time during which the flow of liquid medicine lasts is determined by the amount of liquid medicine injected, the viscosity thereof, elasticity of the rubber-like elastic membrane 31, the inner diameter and the length of the tube 21 of the liquid medicine flow rate control means 20, the pressure in a human body into which the liquid medicine is to be injected, and so on. In practice, the value is obtained by measuring the time required for a certain type of liquid medicine to be forced out of individual continuous liquid medicine injectors 10.

This embodiment has the following advantages.

The liquid medicine flow rate control means 20 employs the tube 21 having an accurately formed inner diameter. So, control of the flow rate of liquid medicine with a high degree of accuracy is ensured by suitably setting the inner diameter and the length of the tube 21. Also, setting of the inner diameter and the length of the tube 21 is made possible by the selection of the inner diameter of the tube 21 and the cutting thereof In consequence, easy mass production is possible, and the production cost of the continuous liquid medicine injector 10 can be reduced.

Furthermore, holes are not formed in the tube 21 by machining, and the tube 21 can be mounted on the liquid medicine injecting portion 15 immediately before use, eliminating a problem involving clogging thereof and so on.

Furthermore, this embodiment of the continuous liquid medicine injector 10 has both the functions of accommodating and pressuring/injecting liquid medicine In consequence, it is small in size and has a simple structure It also ensures easy handling of the injector. It does not therefore limit the actions of a patient, alleviates the labor and reduces the time during which an operator has to be restricted. Further, provision of the liquid medicine flow-out prevention means 14 in the liquid medicine receiving portion 13 and the hermetical structure of the overall continuous liquid medicine injector 10 ensure that no air enters the injector 10 until the rubber-like elastic membrane 31 is completely contracted once air has been exhausted out of it.

Furthermore, the rubber-like elastic membrane 31 which serves as a pressurizing means has a simple structure, making the overall injector small in size and light in weight.

The present invention is not limited to the above-described embodiment, but various modifications are possible within the scope of the present invention.

Figure 5A:
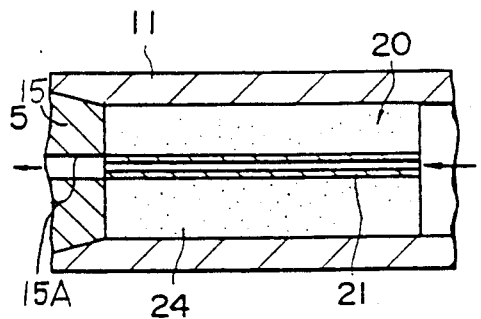
FIGS. 5(A) to 5(F) are enlarged cross-sectional views of the essential parts of modified examples of the present invention.
Figure 5B:
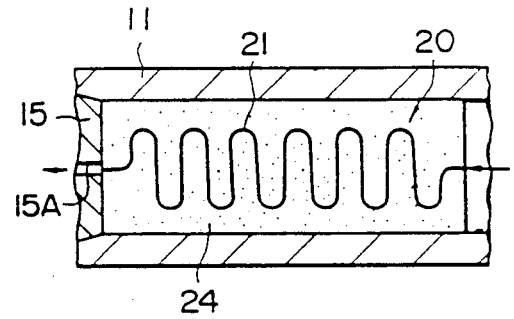
Figure 5C:
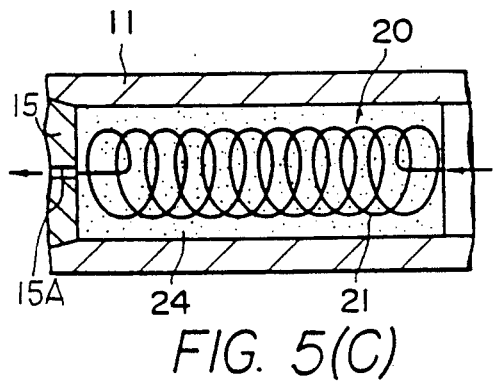
Figure 5D:
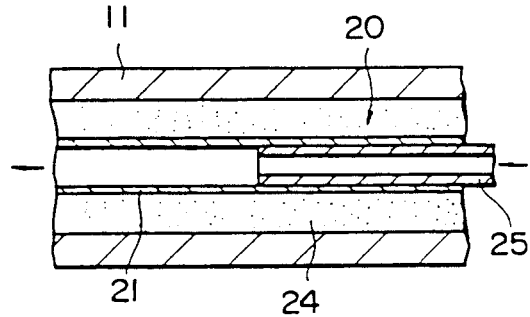
Figure 5E:
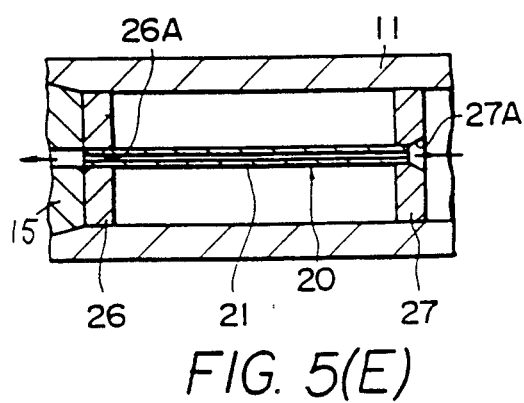
Figure 5F:
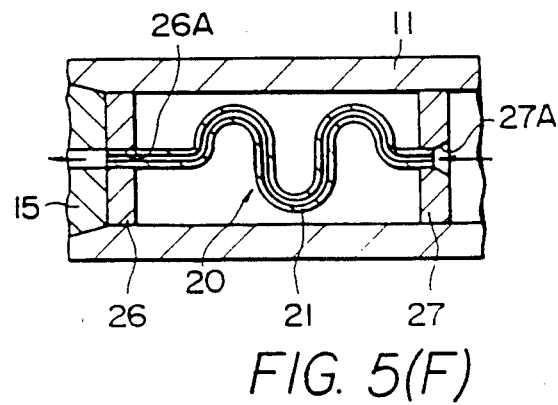

For example, as shown in FIG. 5(A), the liquid medicine flow rate control means 20 may be a tube 21 which is fixed by a synthetic resin layer 24 filled between the inner periphery of the cylindrical body 11 and the outer periphery of the tube 21 and whose one end is made to communicate with a central hole 15A in the liquid medicine injecting portion 15. Alternatively, as shown in FIG. 5(B), the tube of FIG. 5(A) may be formed in a zigzag fashion within the synthetic resin layer 24 so as to make it longer Alternatively, the tube 21 of FIG. 5(A) may be disposed in a helical fashion, as shown in FIG. 5(C), so as to make it longer Further, if a tube 21 having a suitable inner diameter which acts as a liquid medicine flow rate control means 20 is not available, a tube 25 may be mounted within the tube 21, as shown in FIG. 5(D) so as to allow both the tubes 21 and 25 to act as the flow rate control means which controls the flow of the liquid medicine. Further, the liquid medicine flow rate control means 20 may be a tube 21 fixed to the cylindrical body 11 through end plates 26 and 27, as shown in FIG. 5(E). The end plates 26 and 27 are respectively fixed to the two ends of the tube 21 with the ends of the tube 21 being passed through through-holes 26A and 27A formed in the end plates 26 and 27. The tube 21 of FIG. 5(E) may also be formed in a zigzag fashion so as to make it longer, as shown in FIG. 5(F).

The liquid medicine supply means is not limited to the syringe 12 employed in this embodiment but it may be a fixed delivery pump. Further, the opening/closing means is not limited to the cock 40 but it may be a pinch which grips an elastic tube which constitutes the liquid medicine injecting portion 15. Alternatively, the opening/closing means may be a generally employed opening valve.

Furthermore, the instrument inserted into the human body is not limited to the needle 50 employed in this embodiment but it may also be a needle with a flexible tube interposed between the mounting portion 51 and the needle edge 52, or a catheter. Suitable catheters include a venous catheter, a urologic catheter, an alimentary catheter, an obstetric catheter, a cerebral surgical catheter, and so on. In the above-described embodiment, any of various types of instrument mounted on a human body is mounted on the cock 40 which is in turn mounted on the liquid medicine injection portion 15 of the continuous liquid medicine injector 10. However, it may also be directly mounted on the liquid medicine injecting portion 15. In other words, it may be mounted anywhere on the side of the liquid medicine injecting portion.

The disclosed embodiment employs the rubber-like elastic membrane 31 as the pressurizing means. However, other types of pressurizing means may also be used. In this embodiment, the rubber-like elastic membrane 31 is mounted on the intermediate portion of the cylindrical body 11. However, it may also be mounted on one end portion thereof. In that case, it is to be noted that the liquid medicine receiving portion 13 bifurcates from the cylindrical body 11.

Furthermore, in the present embodiment, the interior of the inflating rubber-like elastic membrane 31 and that of the cylindrical body 11 form the liquid medicine accommodating portion 35. However, the liquid medicine accommodating portion 35 is not limited to that, and it may have another structure.

The liquid medicine flow rate control means 20 is not limited to the thin tube 21 but it may also be a porous or penetrating member provided in the liquid medicine injection portion 15, such as an activated carbon, a pumice, resin particles, silica gel or urethane gel. However, use of the porous or penetrating member does not ensure that the flow rate is controlled with the same degree of accuracy as that with which control of the flow rate is performed with the thin tube 21.

As will be understood from the foregoing description, in the present invention, it is possible to control the flow rate of liquid medicine with a high degree of accuracy

What is claimed is:

1. A continuous liquid medicine injector, comprising:
   an injector body formed with a liquid medicine accommodating portion;
   pressurizing means for applying pressure to a liquid medicine accommodated in said liquid medicine accommodating portion; and
   flow rate control means mounted within the injector body and an instrument inserted into a human body through which the liquid medicine in said liquid medicine accommodating portion is forced into a human body by means of the pressure applied by said pressurizing means, wherein said flow rate control means includes a thin tube having a predetermined inner diameter and a predetermined length, the flow rate of the liquid medicine being controlled by the passage of said liquid medicine through said thin tube.

2. A continuous liquid medicine injector according to claim 1, wherein said injector body is a cylindrical body, and further including a liquid medicine receiving portion provided at one end of said cylindrical body, said liquid medicine receiving portion including a liquid medicine flow-out preventing means for preventing the liquid medicine injected from flowing out of said liquid medicine receiving portion.

3. A continuous liquid medicine injector according to claim 2, wherein said liquid medicine flow rate control means for controlling the flow of the liquid medicine is provided at one side of the other end of said cylindrical body and wherein said instrument inserted into the human body is detachably provided on the other side of said other end of said cylindrical body.

4. A continuous liquid medicine injector according to claim 2, wherein an intermediate portion of said cylindrical body has a through-hole, said through-hole being covered by a cylindrical rubber-like elastic film whose two end portions are closely fixed to said cylindrical body and whose intermediate portion can be separated from said cylindrical body, the liquid medicine injected into said cylindrical body from said liquid medicine receiving portion being caused to flow into said rubber-like elastic film through said through-hole to inflate said rubber-like elastic film, the inflating force of said rubber-like elastic film constituting said liquid medicine pressurizing means.

5. A continuous liquid medicine injector according to claim 2, wherein said liquid medicine accommodating portion is defined by an interior of said rubber-like elastic film which has been inflated and an interior of said cylindrical body.

6. A continuous liquid medicine injector according to claim 2, wherein said thin tube is bonded within a covering tube, said thin tube being fixed to said cylindrical body through said covering tube.

7. A continuous liquid medicine injector according to claim 2, wherein said thin tube is fixedly buried within a synthetic resin filling a portion of said cylindrical body.

8. A continuous liquid medicine injector according to claim 2, wherein said thin tube is supported by plates disposed within said cylindrical body spaced apart from each other at a predetermined interval.

9. A continuous liquid medicine injector according to claim 2, wherein said thin tube is made of one of a resin, a metal or a ceramic.

10. A continuous liquid medicine injector according to claim 3, further including an opening/closing means interposed between said liquid medicine flow rate control means and said instrument inserted into the human body for suitably blocking the flow of the liquid medicine.

11. The injector of claim 7, wherein said thin tube is disposed in a zig-zag fashion in the resin.

12. The injector of claim 7, wherein said thin tube is helically arranged in the resin.

13. The injector of claim 8, wherein said tube extends in a zig-zag fashion between the plates.

* * * * *

UNITED STATES PATENT AND TRADEMARK OFFICE
CERTIFICATE OF CORRECTION

PATENT NO. : 4,998,918
DATED : March 12, 1991
INVENTOR(S) : Shinji MIMURA

It is certified that error appears in the above-identified patent and that said Letters Patent is hereby corrected as shown below:

On the Title Page:

After "[22] Filed: Jun. 30, 1989" insert the priority data as follows:

--[30]    Foreign Application Priority Data
          May 22, 1989 [JP]    Japan......1-129931--

Signed and Sealed this

Twenty-eighth Day of December, 1993

Attest:

BRUCE LEHMAN

Attesting Officer    Commissioner of Patents and Trademarks